(12) United States Patent
Ford et al.

(10) Patent No.: US 8,307,541 B2
(45) Date of Patent: Nov. 13, 2012

(54) ASSEMBLY FOR PLACING AN INSERT INTO COMMUNICATION WITH AN ANALYTICAL CHEMICAL INSTRUMENT

(75) Inventors: Douglas W. Ford, West Linn, OR (US); Robert DeLine, Corbett, OR (US)

(73) Assignee: Optimize Technologies, Inc., Oregon City, OR (US)

( * ) Notice: Subject to any disclaimer, the term of this patent is extended or adjusted under 35 U.S.C. 154(b) by 498 days.

(21) Appl. No.: 12/646,390

(22) Filed: Dec. 23, 2009

(65) Prior Publication Data

US 2010/0154207 A1    Jun. 24, 2010

Related U.S. Application Data

(60) Provisional application No. 61/140,571, filed on Dec. 23, 2008.

(51) Int. Cl.
*B23P 19/00* (2006.01)
(52) U.S. Cl. ............. 29/700; 29/801; 29/234; 29/281.1; 29/282; 29/464; 29/468; 29/469
(58) Field of Classification Search .................... 29/700, 29/723, 801, 213.1, 234, 237, 238, 281.1, 29/282, 464, 468, 469; 210/249
See application file for complete search history.

(56) References Cited

U.S. PATENT DOCUMENTS

| | | | |
|---|---|---|---|
| 3,219,416 A | 11/1965 | Natelson | |
| 3,499,733 A | 3/1970 | Abbott | |
| 3,570,555 A | 3/1971 | Gilson | |
| 4,131,426 A | 12/1978 | Range | |
| 4,314,736 A | 2/1982 | Demnianiuk | |
| 4,478,715 A * | 10/1984 | Goodnight, Jr. | ........... 210/198.2 |
| 4,732,672 A * | 3/1988 | Kiang et al. | ............... 210/198.2 |
| 4,845,025 A | 7/1989 | Lary | |
| 5,334,349 A | 8/1994 | Kelln | |

(Continued)

FOREIGN PATENT DOCUMENTS

DE       4029996 A1 *  3/1992
KR   10-2008-0066711 A   7/2008

OTHER PUBLICATIONS

International Search Report and Written Opinion dated Aug. 17, 2010, issued in corresponding International Application No. PCT/US2009/069463, filed Dec. 23, 2009, 10 pages.

*Primary Examiner* — Essama Omgba
(74) *Attorney, Agent, or Firm* — Christensen O'Connor Johnson Kindness PLLC

(57) ABSTRACT

An assembly for placing an insert into communication with an analytical chemical instrument having a first portion of tubing and a second portion of tubing includes a clamp arm assembly having first and second opposable clamp arms and a first fitting subassembly in communication with the first portion of tubing and configured to engage a first portion of an insert, wherein the first fitting subassembly is received within the first clamp arm. The assembly further includes a second fitting subassembly in communication with the second portion of tubing and configured to engage a second portion of the insert, wherein the second fitting subassembly is moveably received within the second clamp arm and biased in a direction toward the first fitting subassembly. Further included is an actuator assembly configured to move the second clamp arm toward the first clamp arm to secure the insert between the first and second fitting subassemblies.

21 Claims, 4 Drawing Sheets

U.S. PATENT DOCUMENTS

| | | |
|---|---|---|
| 5,518,693 A | 5/1996 | Tomasso |
| 5,585,068 A | 12/1996 | Panetz |
| 5,601,707 A | 2/1997 | Clay |
| 7,575,676 B2 * | 8/2009 | Prentice et al. ............ 210/198.2 |
| 7,909,367 B2 * | 3/2011 | Plant et al. .................... 285/249 |
| 2008/0014576 A1 | 1/2008 | Jovanovich |
| 2008/0237112 A1 | 10/2008 | Ford |
| 2012/0012719 A1 * | 1/2012 | Manke et al. .............. 248/219.4 |

* cited by examiner

ASSEMBLY FOR PLACING AN INSERT INTO COMMUNICATION WITH AN ANALYTICAL CHEMICAL INSTRUMENT

CROSS-REFERENCE TO RELATED APPLICATION

This application claims the benefit of U.S. Patent Application No. 61/140,571, filed on Dec. 23, 2008, the disclosure of which is hereby expressly incorporated herein by reference.

BACKGROUND

High performance liquid chromatography (or high pressure liquid chromatography, HPLC) and ultra high performance liquid chromatography (UHPLC) are both a form of column chromatography used frequently in biochemistry and analytical chemistry to separate, identify, and quantify compounds. HPLC and UHPLC utilize an HPLC column that holds chromatographic packing material (stationary phase), a pump that moves the mobile phase(s) through the HPLC column, and a detector that shows the retention times of the molecules. Retention time varies depending on the interactions between the stationary phase, the molecules being analyzed, and the solvent(s) used. In HPLC analysis, the sample is pumped through the HPLC column under an elevated pressure, typically at 300 to 6,000 psi, and in UHPLC, analysis, system pressure extends upward to 1400 bar or 20,000 psi or higher.

Liquid chromatography-mass spectrometry (LC/MS) is an analytical chemistry technique that combines the physical separation capabilities of liquid chromatography with the mass analysis capabilities of mass spectrometry. LC/MS is a powerful technique used for many applications which has very high sensitivity and specificity. Generally its application is oriented towards the specific detection and potential identification of chemicals in the presence of other chemicals (in a complex mixture).

Often a sample bound for HPLC, UHPLC, or LC/MS analysis requires some type of clean-up to ensure optimal results. Detergents or salts can affect the ionization process, while overly dilute samples can be swamped out by background noise, making them undetectable. Trap columns are small packed beds that use the adsorptive properties of analytes to effectively concentrate dilute samples, desalt, remove detergents, and more. Trap columns have the advantage of being able to be used in a completely on-line environment. The trap column is normally of a certain design and material specifically suited for a certain compound or class of compounds. For instance, Optimize Technologies offers two lines of trap columns to suit trapping needs. The OPTI-PAK® capillary traps are designed for ultra-low volume applications where any excess in volume could be detrimental to the assay. OPTI-LYNX™ traps offer higher capacity. Both formats are available in a number of different phases and support materials such that a user may choose the trap design and material that best fits the situation.

All of the various components and lengths of tubing used in HPLC, UHPLC, and LC/MS analysis are typically interconnected by fitting assemblies, such as those described in prior patents and pending applications, for example, U.S. Pat. Nos. 5,525,303; 5,669,637; 5,730,943; 5,911,954; 6,000,916; and 6,095,572, and U.S. patent application Ser. No. 11/971,834, filed on Jan. 9, 2008, the disclosures of which are herein all incorporated by reference herein. For instance, the fitting assemblies may include a first and second fitting subassembly that receives an insert therebetween, such as a column, to place the column into fluid communication with the tubing. It is advantageous if the fitting assembly provides a true zero-dead-volume connection between the analytical components to minimize dead space in the flow path. Moreover, it is beneficial to minimize the tubing length required to couple the column to the analytical instrument. Adding tubing length to the connection significantly degrades the analysis, for example, by adding band broadening.

Moreover, during HPLC, UHPLC, and LC/MS analysis, it is desirable to be able to quickly change the HPLC columns, the trap columns, or other columns being used when, for example, the column needs to be removed for maintenance or reconfiguration. Moreover, the column often needs to be replaced with a different column having a certain design, dimension, or packing material specifically suited for a certain compound or class of compounds. Columns must also be replaced when they become saturated or contaminated.

Changing the column requires the operator to manually disconnect the fitting assembly and replace the column. This time-consuming process decreases throughput and efficiency. This is especially true when the sample being analyzed is a dangerous substance that requires the use of a glove box or another suitable enclosed area. Thus, it is desired to provide an efficient, automated process and apparatus for changing/replacing columns in an HPLC, UHPLC, LC/MS, or a similar analytical system with minimal disruption. Moreover, it is desirable that the apparatus be suitable for a small space so that the apparatus may be placed in a location that minimizes the length of tubing needed in the system.

SUMMARY

An assembly for placing an insert into communication with an analytical chemical instrument having a first portion of tubing and a second portion of tubing includes a clamp arm assembly having first and second opposable clamp arms and a first fitting subassembly in communication with the first portion of tubing and configured to engage a first portion of an insert, wherein the first fitting subassembly is received within the first clamp arm. The assembly further includes a second fitting subassembly in communication with the second portion of tubing and configured to engage a second portion of the insert, wherein the second fitting subassembly is moveably received within the second clamp arm and biased in a direction toward the first fitting subassembly. Further included is an actuator assembly configured to move the second clamp arm toward the first clamp arm to secure the insert between the first and second fitting subassemblies.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
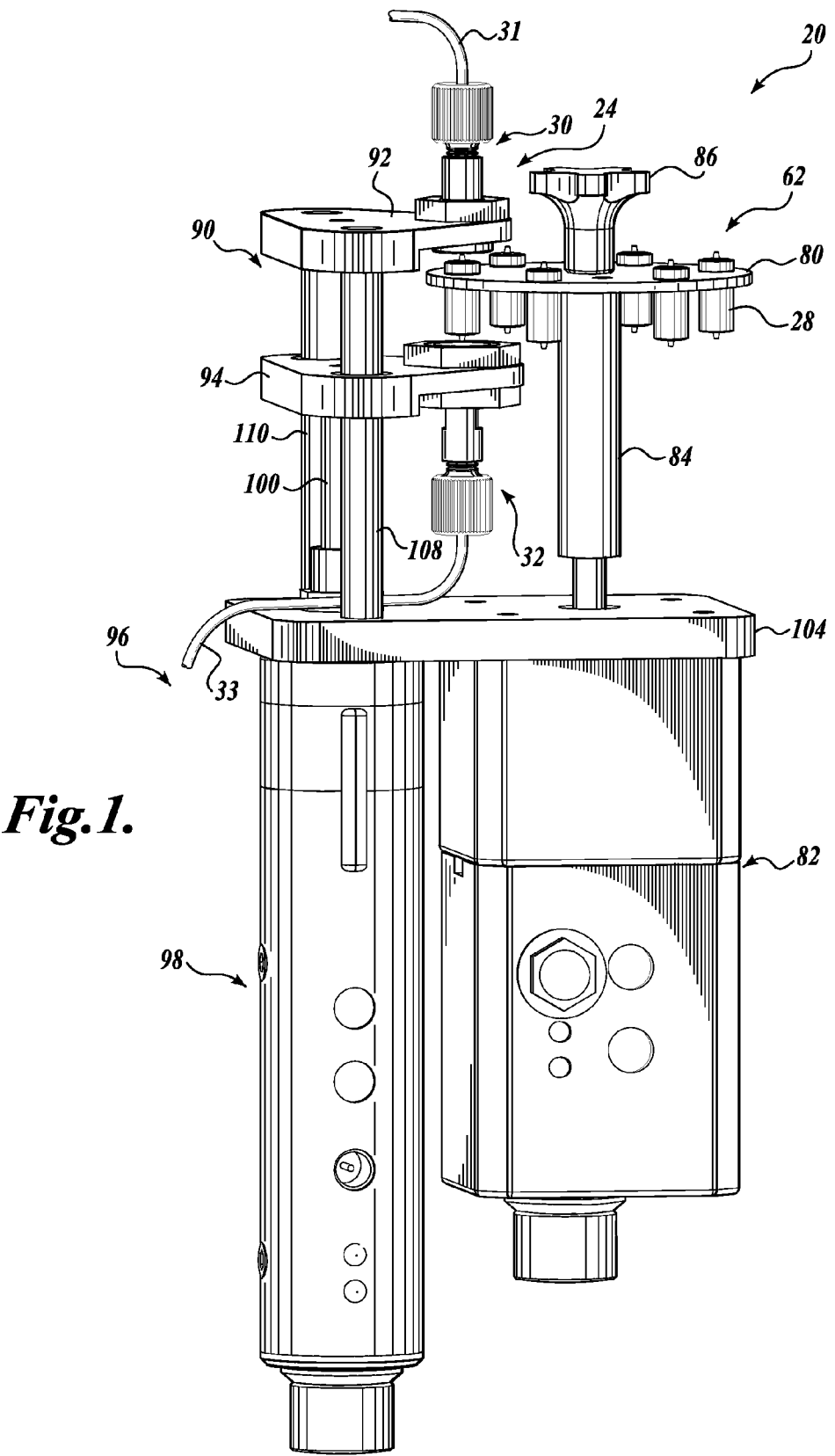
FIG. 1 is an isometric view of an automated column changer formed in accordance with one embodiment of the present disclosure, wherein the automated column changer is shown in a first position.

Referring to FIG. 1, a first embodiment of an assembly for placing an insert into communication with an analytical chemical instrument is depicted. The first embodiment is in the form of an automated column changer 20, which is capable of automatically mating and unmating an insert, such as a column, to an HPLC or UHPLC fitting assembly of an HPLC or UHPLC analytical chemical instrument. Although the automated column changer 20 will be hereinafter described with reference to HPLC and UHPLC systems (hereinafter collectively referred to as "U/HPLC") used in the analysis or purification of chemical compounds, it should be appreciated that the automated column changer 20 may be used with any suitable system, such as LC/MS systems. Moreover, it should be appreciated that the automated column changer maybe used in any suitable application requiring the use of a pressure between about 0 psi and 30,000 psi, or even higher.

The automated column changer 20 includes a column positioning assembly suitable for receiving and storing columns 28 and positioning the columns 28 in a specific indexed position for replacement within a U/HPLC fitting assembly 24 of the U/HPLC analytical chemical instrument. In the first embodiment, the column positioning assembly is in the form of a carousel assembly 62 suitable for moving the columns into a specific indexed rotational position for replacement within the U/HPLC fitting assembly 24. The automated column changer 20 further includes a clamp assembly 90 configured to selectively secure the U/HPLC fitting assembly 24 onto the columns 28 when the columns are properly positioned between the portions of the U/HPLC fitting assembly 24 for replacement.

A brief description of the U/HPLC fitting assembly 24 and the columns 28 receivable within the U/HPLC fitting assembly 24 will be hereinafter provided in order to more clearly understand the description of the automated column changer 20 provided below. However, it should be appreciated that the automated column changer 20 may instead be used to replace or change any suitable insert received within a suitable fitting assembly of an analytical chemical test instrument.

Figure 2A:
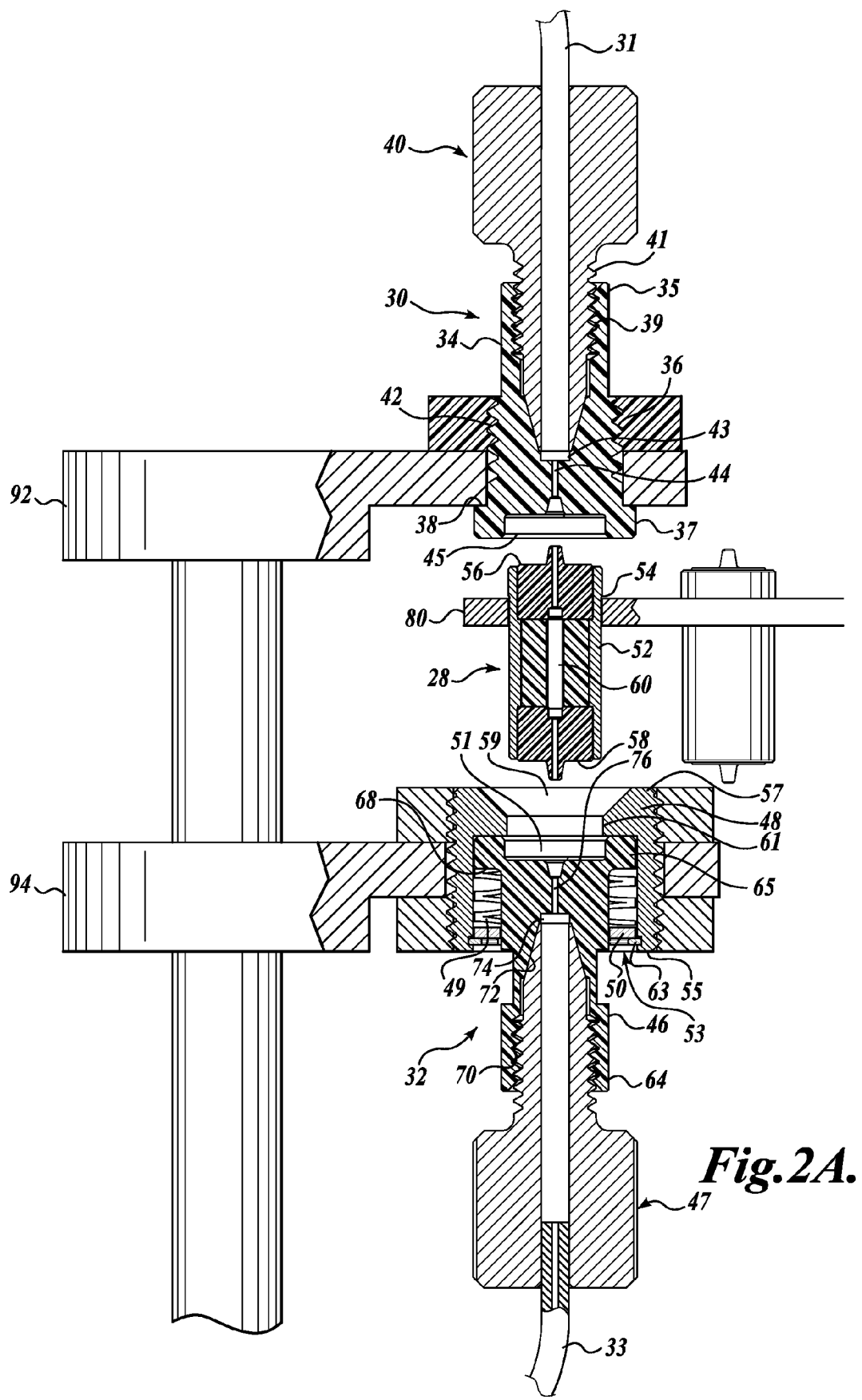
FIG. 2A is a partial cross-sectional side view of a portion of the automated column changer of FIG. 1, wherein the automated column changer is shown in the first position.
Figure 2B:
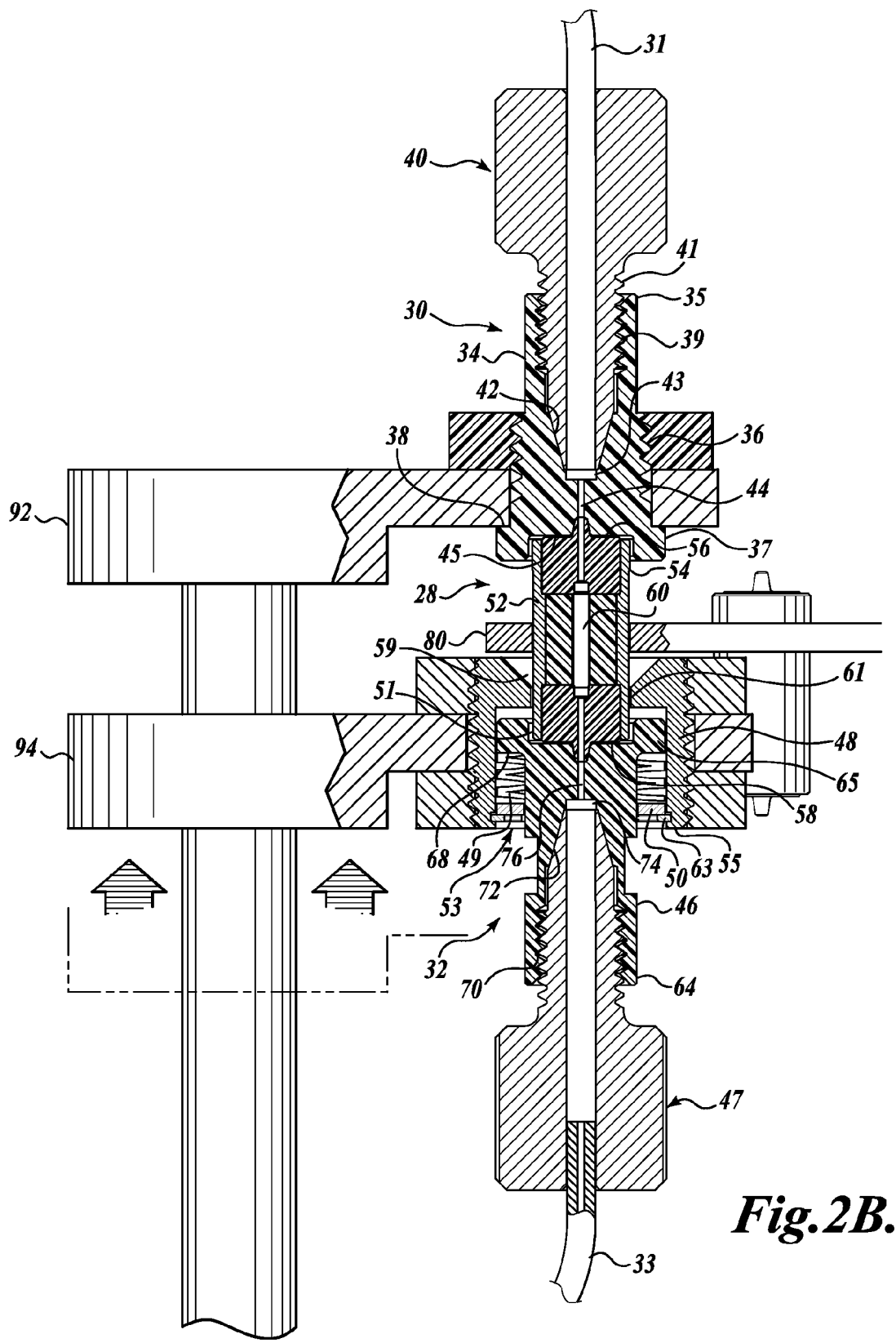
FIG. 2B is a partial cross-sectional side view of a portion of the automated column changer of FIG. 1, wherein the automated column changer is shown in a second position.

Referring to FIG. 2A, the U/HPLC fitting assembly 24 includes a first fitting subassembly 30 connected to a first portion of tubing 31 and a second fitting subassembly 32 connected to a second portion of tubing 33. The first fitting subassembly 30 is comprised of a first fitting 34 having a tubular body with first and second ends 35 and 37 and a central passageway extending between the first and second ends 35 and 37. The external diameter of the second end 37 is greater than the external diameter of the first end 35 such that an external annular shoulder 38 is defined near the second end 37 of the first fitting 34. The second end 37 of the first fitting 34 may include a knurled outer surface to facilitate gripping and turning the first fitting 34.

The first fitting 34 includes an externally threaded portion 36 formed at its second end 37 that is threadably engageable with a substantially transverse first clamp arm 92 of the clamp assembly 90. The first clamp arm 92 threadably receives the first fitting 34 of the first fitting subassembly 30 such that the shoulder 38 of the first fitting 34 abuts the bottom surface of the first clamp arm 92.

A first fluid conduit 40 is threaded coupled to the first end 35 of the first fitting 34 such that it extends upwardly from the first fitting 34 and the first clamp arm 92. More specifically, the central passageway of the first fitting 34 includes an internally threaded portion 39 formed at its first end 35 that is designed for receiving an externally threaded mating coupling 41 of the first fluid conduit 40. The central passageway of the first fitting 34 narrows in diameter at its distal terminus to form a tapered chamber 42, which extends from the internally threaded portion 39 towards the second end 37 of the first fitting 34.

The tapered chamber 42 has a frustoconical sealing surface that seals against a conventional ferrule (not shown) received coaxially on the distal tip of the first portion of the tubing 31 or otherwise formed on the distal tip end of the first fluid conduit 40. The tapered chamber 42 further narrows to form a cylindrical chamber 43 which extends from the tapered chamber 42 into the second end 37 of the first fitting 34. The cylindrical chamber 43 forms a "tube stop" that closely and fully receives the distal tip of the fluid conduit 40 and/or the first portion of tubing 31. The cylindrical chamber 43 further narrows to form a small diameter passage 44 extending from the cylindrical chamber 43 to a centrally-located female fitting cavity 45 formed in the second end 37 of the first fitting 34. The passage 44 is sized to correspond to the internal diameter of the first portion of the tubing 31 received within the first fluid conduit 40, for a zero-dead volume connection.

The second fitting subassembly 32 similarly includes a second fitting 46 threadably coupled to a second fluid conduit 47, wherein the second fitting 46 and second fluid conduit 47 are substantially similar to the first fitting 34 and the first fluid conduit 40 described above. More specifically, the second fitting 46 includes a tubular body with first and second ends 64 and 65 and a central passageway extending between the first and second ends 64 and 65. The external diameter of the second end 65 is greater than the external diameter of the first end 64 such that an external annular shoulder 68 is defined near the second end 65 of the second fitting 46.

The central passageway of the second fitting 46 includes an internally threaded portion 70 formed at the first end 64 of the second fitting 46 that is designed for receiving an externally threaded mating coupling 41 of the second fluid conduit 47. The central passageway of the second fitting 46 narrows in diameter at its distal terminus to form a tapered chamber 72 that narrows to form a cylindrical chamber 74, as described above with respect to the first fitting subassembly 30. The cylindrical chamber 74 forms a "tube stop" that closely and fully receives the distal tip of the fluid conduit 47 and/or the second tubing portion 33. The cylindrical chamber 74 further narrows to form a small diameter passage 76 extending from the cylindrical chamber 74 to a centrally-located second female fitting cavity 51 formed in the second end 65 of the second fitting 46. The passage 76 is sized to correspond to the internal diameter of the second portion of the tubing 33 received within the second fluid conduit 47 for a zero-dead volume connection.

Unlike the first fitting 34 described above, the second fitting 46 does not include an externally threaded portion formed at its second end 65. Rather, the second fitting 46 has a non-threaded outer surface such that its second end 65 may be moveably received within a portion of a hollow nut 48 that is secured within a second clamp arm 94, such as by threaded engagement. The hollow nut 48 includes first and second ends 55 and 57 and a central opening extending between the first and second ends 55 and 57. The central opening includes a first cylindrical opening portion 53 defined at the first end 55 of the nut 48 that is sized and shaped to slidably receive and retain the second end 65 of the second fitting 46 within the nut 48, including the enlarged end portion defining the annular shoulder 68. The second end 65 of the second fitting 46 can move linearly up and down along the center axis of the nut central opening.

The second fitting 46 may be either rotatable with respect to the nut 48 or it may instead be limited to only linear movement within the nut 48. If it is desirous that the second fitting 46 be capable of rotating with respect to the nut 48, the cross-sectional shape of both the second end 65 of the second fitting 46 and the nut central opening may be circular to allow for both linear and rotational movement. Instead, the second end 65 of the second fitting 46 and the nut central opening may be correspondingly polygonal-shaped such that the second fitting 46 can move linearly with respect to the nut 48 but cannot rotate with respect to the nut 48.

The central opening of the nut 48 further includes a tapered opening portion 59 defined at the second end 57 of the nut 48 that is configured to guide a column 28 downwardly into a second cylindrical opening portion 61 sized and configured to slidably receive the column 28. The second cylindrical opening portion 61 extends between the tapered opening portion 59 and the cylindrical opening portion 53. The tapered opening portion 59, second cylindrical opening portion 61, and the first cylindrical opening portion 53 are concentrically located within the nut 48. As such, when a column 28 is either dropped into the tapered opening portion 59 or the nut 48 is moved upwardly into engagement with a column 28, the column 28 is received within the second and first cylindrical openings 61 and 53 until the column 28 engages and is received within the second female fitting cavity 51 in the second fitting 46.

The second fitting 46 is retained within the first cylindrical opening 53 of the nut 48 by a biasing member 49, such as a spring, that is retained within the first cylindrical opening 53 by a support washer 50 and annular seal 63. The biasing member 49 is disposed between the washer 50 and the annular shoulder 68 to continuously urge the second fitting 46 into engagement with the column 28.

Referring to FIG. 2A, a description of the column 28 configured to mate with the first and second fitting subassemblies 30 and 32 to define the U/HPLC fitting assembly 24 for use in an U/HPLC analytical chemical instrument will be hereinafter provided. It should be appreciated that any suitable column may be used; and therefore, the following description should not be seen as limiting the scope of the present disclosure. Each column 28 includes a hollow cylindrical body 52 that is made of a suitable material well known in the art. The cylindrical body 52 includes an upper portion of increased outer diameter to define an annular shoulder 54 on the exterior surface of the cylindrical body 52.

First and second male fittings 56 and 58 are sealingly received in the upper and lower open ends of the cylindrical body 52 by any suitable means, such as by a friction fit. The shape and size of the protruding portions of the first and second male fittings 56 and 58 substantially correspond to the shape and size of the first and second female fitting cavities 45 and 51 defined within each of the first and second fittings 34 and 46. In this manner, the first and second male fittings 56 and 58 are receivable within the first and second female fitting cavities 45 and 51 when the U/HPLC fitting assembly 24 is assembled. The first and second male fittings 56 and 58 each include input and output openings that are in communication with the small diameter passage 44 of the first and second fittings 34 and 46 when the first and second male fittings 56 and 58 are received within the first and second female cavities 45 and 51. The input and output openings of the first and second male fittings 56 and 58 are also in communication with a central passageway extending through the column 28.

A packing material (or separating media) 60 is disposed within the central passageway of the column 28. The packing material 60 may be a particulate packing material through which particles greater than a predetermined size are prevented from passing. Alternately, the packing material may be a chemical packing material, such as a selectively absorbent or adsorbent packing material that filters out substances having specific chemical properties. It should be appreciated that any known packing material suitable for selectively filtering fluids passing therethrough can be included without departing from the scope of the disclosure. Each column 28 may include a different packing material 60 that is specifically suited for a certain compound or class of compounds.

Referring to FIGS. 1 and 2A, the carousel assembly 62 suitable for receiving and storing columns 28 and positioning the columns 28 for replacement within the U/HPLC fitting assembly 24 will now be described. In general, the carousel assembly 62 rotates columns 28 into a specific indexed rotational position for replacement of the column 28 within the first and second fitting subassemblies 30 and 32 of the U/HPLC fitting assembly 24, which may be referred to as the "reloading position."

The carousel assembly 62 includes a plate 80 that is preferably circular in shape and includes openings or slots formed along its outer circumference that are suitable for receiving and retaining columns 28 therein. The openings in the plate 80 may be of substantially the same diameter as the column 28 such that the upper surface of the plate 80 engages the annular shoulder 54 formed on the column 28 when the column 28 is dropped into the opening. As such, gravity secures the column 28 within the plate 80. Preferably, the openings are spaced equidistant from one another along the outer circumference of the plate 80 and spaced radially inwardly from the outer circumference a predetermined distance. In this manner, indexed rotation of the plate 80 positions each column 28 in the reloading position between the first and second fitting subassemblies 30 and 32 of the U/HPLC fitting assembly 24. It should be appreciated that the columns 28 may be removably secured to the plate 80 in any other suitable manner.

The carousel assembly 62 is driven by a suitable motor 82. Any motor or motor/controller assembly suitable for selectively rotating the plate 80 into one of a plurality of indexed rotational positions in one of first and second directions may be used. The plate 80 is transversely and concentrically mounted to an end of an output shaft 84 of the motor 82. The plate 80 is preferably removably secured to the output shaft 84 such that the entire plate 80 may be removed for reconfiguration or replacement of the columns 28. The plate 80 may also be removed if, for instance, it is desired to manually change or position the column 28 within the U/HPLC fitting assembly 24. A threaded knob 86 may be passed through a central opening in the plate 80 and thereafter threaded into an opening in the output shaft 84 to removably secure the plate 80 onto the output shaft 84.

Referring back to FIG. 1, the clamp assembly 90 having first and second opposing clamp arms 92 and 94 that selectively secure the first and second fitting subassemblies 30 and 32 onto the column 28 will now be described. As noted above, the first clamp arm 92 threadably receives the first fitting 34 of the first fitting subassembly 30 such that the first fluid conduit 40 extends upwardly from the first clamp arm 92 and the shoulder 38 of the first fitting 34 abuts the bottom surface of the first clamp arm 92. Moreover, the second clamp arm 94 threadably receives the nut 48 of the second fitting subassembly 32 such that the second fluid conduit 47 extends downwardly from the second clamp arm 94 and the nut 48 is substantially flush with the upper surface of the second clamp arm 94.

The first and second fitting subassemblies 30 and 32 are received within the first and second opposing clamp arms 92 and 94 to engage and compress a column 28 when the column 28 is positioned therebetween in the reloading position. To engage the column 28, the second clamp arm 94 is moved upwardly until the second fitting 46 engages the column 28. The second male fitting 58 is received into the female fitting cavity 36 of the second fitting 46 and the column 28 is lifted out from within the plate 80. The column 28 moves upwardly with the second clamp arm 94 and second fitting 76 until the column 28 engages the first fitting 34. The first male fitting 56 of the column 28 is then received into the female fitting cavity 36 of the first fitting 34. The spring-loaded second fitting 46 helps compress the column 28 between the first and second fittings 34 and 46 to create a seal capable of resisting leakage of low or high pressure fluid pumped through the column 28, the first and second fitting subassemblies 30 and 32, and the first and second portions of tubing 31 and 33. The spring-loaded second fitting 46 also helps ensure a zero dead volume connection between the first fitting subassembly 30, the column 28, and the second fitting subassembly 32.

The clamp assembly 90 is operably coupled to a linear actuator assembly 96 for selectively moving the second clamp arm 94 up and down to move the U/HPLC fitting assembly 24 into and out of engagement with a column 28. Although any suitable linear actuator assembly or other drive assembly may be used to move the second clamp arm 94, the linear actuator assembly 96 preferably includes an actuator cylinder 98 having a push rod 100 slidably received within the actuator cylinder 98. The actuator cylinder 98 is mounted to a bracket 104, which is also coupled to the motor 82 such that the actuator cylinder 98 and the motor 82 are fixed relative to one another. The linear actuator assembly 96 may include limit switches (not shown) that shut the actuator assembly 80 off in the extended and retracted positions.

The push rod 100 of the linear actuator assembly 96 is coupled to the second clamp arm 94 such that the extension and retraction of the push rod 100 moves the second clamp arm 94 up and down. Extending upwardly from the bracket 104 are first and second slide rods 108 and 110 that pass through the second clamp arm 94 and are secured at their upper ends to the first clamp arm 92. As such, the first clamp arm 92 is in a fixed position relative to the second clamp arm 94. Moreover, the second clamp arm 94 is slidably received on the first and second slide rods 108 and 110 such that the second clamp arm 94 is moveable by the push rod 100 with respect to the first clamp arm 92. The push rod 100 is actuated to move the second clamp arm 94 up and down along the slide rods 86 and 88 to open and close the U/HPLC fitting assembly 24.

Any suitable actuation force may be used to open and close the U/HPLC fitting assembly 24 and suitably compress the column 28 between the first and second fittings 34 and 46 to prevent leakage and ensure a zero dead volume connection. For instance, for an HPLC system at 6,000 psi, the actuation force may be about 6.87 lbs. For a UHPLC system at 20,000 psi, the actuation force may be about 22.9 lbs. It should be appreciated that the actuation force may be adjusted to correspond to any suitable pressure application being used.

The linear actuator assembly 96 and motor 82 may be either manually operated through mechanical force or through interaction with an electronic interface device, such as through a suitable programmable logic controller (PLC). The PLC may be integrated within the automated column changer 20, or it may instead be integrated within a PC type computer (not shown). The PLC receives input from a plurality of sensors (not shown) mounted within the automated column changer 20, such as position sensors or sensors for detecting events, errors, and failures. The PLC may further receive input from a user interface such as a computer (not shown). The sensor data and the signals from the computer are processed by the PLC, which outputs appropriate control signals to control the operation and timing of the automated column changer components.

For instance, when the user interfaces with a software package on a computer to select a column 28 for the U/HPLC fitting assembly 24, the PLC outputs signals to drive the linear actuator assembly 96 to move the second clamp arm 94 downwardly away from the first clamp arm 92 to disengage the U/HPLC fitting assembly 24 from the column 28 currently being used. The PLC also outputs signals to drive the motor 82 to rotate the carousel assembly 62 to position the desired column 28 between the first and second clamp arms 92 and 94 for replacement. Signals are then outputted to drive the linear actuator assembly 96 to move the second clamp arm 94 toward the first clamp arm 92 to engage the U/HPLC fitting assembly 24 with the new column 28. When it is desired to change or replace the column, the user then interfaces with the software package to select the next column for use. It should be appreciated that the column changing and replacement may automatically occur upon the detection of certain events by the system sensors.

In view of the foregoing, it can be seen that the automated column changer 20 provides a system and method for quickly and automatically mating and unmating a column to an analytical testing device. Moreover, with the automated column changer 20 having a relatively compact, small footprint, as can be seen in FIG. 1, the automated column changer 20 can be used in small spaces, such as in a glove box, and oven, etc., and the length of tubing required for the connection is minimized.

It should also be appreciated that the automated column changer 20 could be modified to include multiple U/HPLC fitting assemblies operably coupled to one or more clamp assemblies and engageable with columns of one or more carousel assemblies to accommodate simultaneous processing of columns. For instance, while a first column is mated with a first U/HPLC fitting assembly to receive a sample stream, a second column may be mated with a second U/HPLC fitting assembly to undergo a preparation treatment, such as purging fluids. At the completion of this step, the second column, now properly prepped, is rotated and mated to the first U/HPLC fitting assembly carrying the sample stream, and a third column is rotated to mate with the second U/HPLC fitting assembly configured to receive the preparation treatment stream.

Moreover, it should be appreciated that the U/HPLC analytical chemical instrument may use two or more automated column changers 20 for performing steps of an analytical process that may be automated by a computer. For example, one could do sample enrichment followed by cation exchange. The samples would be pushed through a column in one direction and then eluted off in reverse followed by a cation exchange step by running the concentrated sample through a cation exchange column. A second sample may need to be analyzed with a "mixed mode" approach by utilizing cation exchange followed by reverse phase followed by an amino column. These processes could be done automatically with the use of two or more automated column changers.

It should further be appreciated that the automated column changer 20 may instead be used without a carousel assembly 62 for situations where the operator desires to change the columns manually one at a time. In this case, the operator could manually drop the column 28 into the second fitting 46 and thereafter actuate the clamp assembly 90 (either manually or through a PLC) to engage the column 28 with the first fitting 34. Use of the automated column changer 20 in this manner prevents the operator from having to use tools or other means to connect the column inline to the U/HPLC analytical chemical instrument. Connecting the components of the first and fitting subassemblies 30 and 32 can be very difficult, especially at very high pressures, such as in UHPLC applications. Moreover, the threaded components can be subject to thread galling when a high amount of torque is required to make the connections, which can result in the threaded components fusing together. Thus, the use of the first and second fitting subassemblies 30 and 32 secured within a clamp arm assembly 90 (that is actuated either manually or automatically) to interchange even a single column can save an operator time and prevent U/HPLC fitting connections failures.

Figure 3:
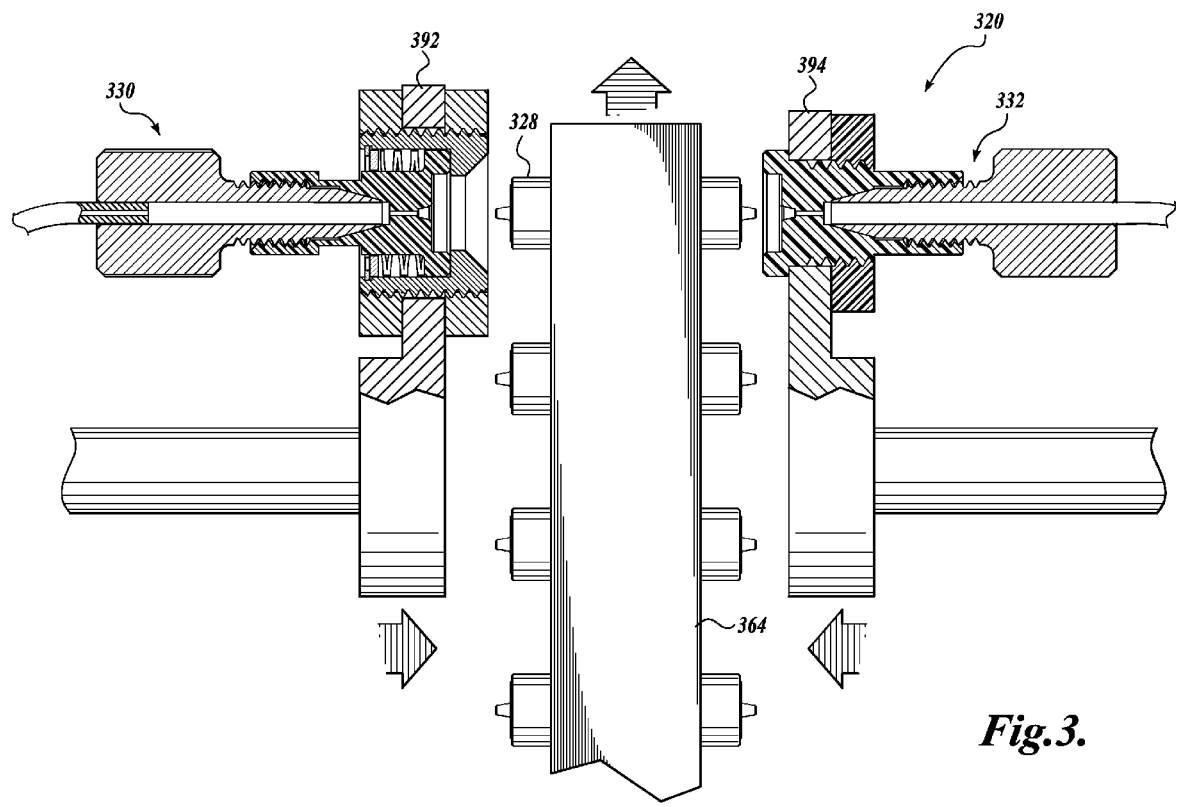
FIG. 3 is a partial cross-sectional side view of a portion of the automated column changer formed in accordance with a second embodiment of the present disclosure, wherein the automated column changer is shown in a first position.

Referring to FIG. 3, an alternate embodiment of an automated column changer 320 configured to linearly feed columns 328 into a reloading position for replacement within a U/HPLC fitting assembly is depicted. Linearly arranging the columns 328 may allow the user to increase the number of columns available for use in the automated column changer 320 and/or provide a system more amenable to parallel processing of the columns.

The automated column changer 320 includes a column positioning assembly embodied as a cartridge 364 that suitably stores and positions columns 328 in a substantially parallel arrangement, wherein the columns 328 are substantially similar to the columns 28 described above or any other suitable design. The cartridge 364 may be any suitable flexible or rigid medium that includes transverse openings or slots suitable to receive the columns 328 therein.

The columns 328 are linearly fed into a reloading position between first and second opposing fitting subassemblies 330 and 332 that are substantially identical to the first and second fitting subassemblies 30 and 32 described above. The first and second fitting subassemblies are received within first and second opposing clamp arms 392 and 294 in substantially the same manner as that described above with respect to the first and second fitting subassemblies 30 and 32 and first and second clamp arms 92 and 94. The first and second fitting subassemblies 330 and 332 are moved towards the column 328 by first and second clamp arms 392 and 394, which may be actuated between extended and retracted positions by any suitable device, such as by one or more linear actuators as described above. The first and second fitting subassemblies 330 and 332 are engaged with a column 328 to define a leak resistant and true zero dead volume connection between the first and second fitting subassemblies 330 and 332 and the column 328.

The columns 328 may be moveably received within the transverse openings/slots in the cartridge 364 such that only one clamp arm 392 or 394 need move between extended and retracted positions. In other words, with the column 328 moveably received within the cartridge 364, one of the first or second clamp arms 392 or 394 could extend to engage the first or second fitting subassembly 330 or 332 with an end of the column 328 and continue to move the column 328 into engagement with the other of the first or second fitting subassemblies 330 or 332.

The cartridge 364 may be loaded into a machine or suitable device having a motor/transmission assembly that automatically advances the cartridge 364 a predetermined linear distance to place the desired column 328 into a reloading position. As an alternative embodiment, the columns 328 may be received within a belt or other flexible medium that is capable of continuously feeding columns 328 into a reloading position within a U/HPLC fitting assembly. It should be appreciated that the columns 328 may be linearly fed into the reloading position by any suitable device.

While the preferred embodiment of the present disclosure has been illustrated and described, it will be appreciated that various changes can be made therein without departing from the spirit and scope of the claimed subject matter.

The embodiments of the present disclosure in which an exclusive property or privilege is claimed are defined as follows:

1. An assembly for placing an insert into communication with an analytical chemical instrument having a first portion of tubing and a second portion of tubing, the assembly comprising:
   (a) a clamp arm assembly having first and second opposable clamp arms;
   (b) a first fitting subassembly in communication with the first portion of tubing and configured to engage a first portion of an insert, the first fitting subassembly received within the first clamp arm;
   (c) a second fitting subassembly in communication with the second portion of tubing and configured to engage a second portion of the insert, the second fitting subassembly moveably received within the second clamp arm and biased in a direction toward the first fitting subassembly; and
   (d) an actuator assembly configured to move the second clamp arm toward the first clamp arm to secure the insert between the first and second fitting subassemblies.

2. The assembly of claim 1, further comprising an insert positioning assembly having at least first and second openings sized and shaped to removably receive at least first and second inserts therein.

3. The assembly of claim 2, wherein the insert positioning assembly is moveable into at least a first position to locate the first insert between the first and second fitting subassemblies.

4. The assembly of claim 3, wherein the insert positioning assembly is a carousel assembly with a rotatable plate having a plurality of openings spaced circumferentially around the exterior of the plate that are configured to removably receive a plurality of inserts.

5. The assembly of claim 4, wherein the plate is moveable into at least first and second positions to move at least first and second columns received within the openings into an indexed rotational position between the first and second fitting subassemblies.

6. The assembly of claim 4, wherein each insert includes an annular protrusion engageable with an upper surface of the plate to temporarily secure the inserts within the plate openings.

7. The assembly of claim 6, wherein the inserts are lifted out of engagement with the upper surface of the plate when the second clamp arm is moved toward the first clamp arm and the second fitting subassembly engages the insert.

8. The assembly of claim 3, wherein the insert positioning assembly is a linearly displaceable medium having at least two transverse openings configured to receive at least first and second columns therein.

9. The assembly of claim 8, wherein the linearly displaceable medium is moveable into at least first and second positions to move at least first and second columns received within the transverse openings into an indexed linear position between the first and second fitting subassemblies.

10. The assembly of claim 9, wherein the linearly displaceable medium is a cartridge.

11. The assembly of claim 9, wherein the linearly displaceable medium is a flexible belt.

12. The assembly of claim 1, wherein the insert is a column for use with an analytical test instrument.

13. An automatic column changer for selectively placing a column into communication with first and second portions of tubing of an analytical chemical instrument, the automatic column changer comprising:
   (a) a clamp arm assembly having first and second opposable clamp arms;
   (b) a first fitting subassembly in communication with the first portion of tubing and configured to engage a first end of a column to place the column into fluid communication with the first fitting subassembly, the first fitting subassembly received within the first clamp arm;
   (c) a second fitting subassembly in communication with the second portion of tubing and configured to engage a second end of a column to place the column into fluid communication with the second fitting subassembly, the second fitting subassembly moveably received within the second clamp arm and biased in a direction toward the first fitting subassembly;
   (d) a column positioning assembly having at least first and second openings sized and shaped to removably receive at least first and second columns therein, wherein the insert positioning assembly is moveable into at least a first position to locate the first column between the first and second fitting subassemblies; and
   (e) an actuator assembly configured to move the second clamp arm toward the first clamp arm to compress a column between the first and second fitting subassemblies and place the column into fluid communication with the first and second fitting subassemblies.

14. The automatic column changer of claim 13, wherein the column positioning assembly is a carousel assembly with a rotatable plate having a plurality of openings spaced circumferentially around the exterior of the plate that are configured to removably receive a plurality of columns.

15. The automatic column changer of claim 14, wherein the plate is moveable into at least first and second positions to move at least first and second columns received within the openings into an indexed rotational position between the first and second fitting subassemblies.

16. The automatic column changer of claim 14, wherein each column includes an annular protrusion engageable with an upper surface of the plate to temporarily secure the columns within the plate openings.

17. The automatic column changer of claim 16, wherein the columns are lifted out of engagement with the upper surface of the plate when the second clamp arm is moved toward the first clamp arm and the second fitting subassembly engages the column.

18. The automatic column changer of claim 13, wherein the column positioning assembly is a linearly displaceable medium having at least two transverse openings configured to receive at least first and second columns therein.

19. The automatic column changer of claim 18, wherein the linearly displaceable medium is moveable into at least first and second positions to move at least first and second columns received within the transverse openings into an indexed linear position between the first and second fitting subassemblies.

20. The automatic column changer of claim 19, wherein the linearly displaceable medium is a cartridge.

21. The automatic column changer of claim 19, wherein the linearly displaceable medium is a flexible belt.

* * * * *